United States Patent [19]

Green

[11] Patent Number: 5,037,643
[45] Date of Patent: * Aug. 6, 1991

[54] COSMETIC COMPOSITION

[75] Inventor: Martin R. Green, Buckingham, United Kingdom

[73] Assignee: Unilever Patent Holdings, B.V., Rotterdam, Netherlands

[*] Notice: The portion of the term of this patent subsequent to May 23, 2006 has been disclaimed.

[21] Appl. No.: 326,953

[22] Filed: Mar. 22, 1989

[30] Foreign Application Priority Data

Mar. 23, 1988 [GB] United Kingdom ............... 8806893

[51] Int. Cl.$^5$ ............................................... A61K 7/06
[52] U.S. Cl. .......................................... 424/70; 514/2; 514/21
[58] Field of Search ....................... 424/70; 514/2, 21

[56] References Cited

U.S. PATENT DOCUMENTS 4,139,619  2/1979  Chidsey, III .......................... 424/45
4,832,946  5/1989  Green ..................................... 424/70

FOREIGN PATENT DOCUMENTS 35919     9/1981   European Pat. Off. .
3431266   3/1986   Fed. Rep. of Germany .
59-186911 10/1984  Japan .
8504577  11/1985   World Int. Prop. O. .

OTHER PUBLICATIONS

Oliver, R. F. (1970), "J. Embryol. Exp. Morphol." 23, 219–236.
"British Journal of Dermatology" (1984), 110, 685–689 (Messenger).
"Proceedings of the Society of Experimental and Biological Medicine", 108, 49–61 (Meyer et al.).
Couchman, J. R. and Gibson, W. T. (1985), "Dev. Biol.", 108, 290–298.
Montagna W. et al., (1952) "Q. J. Microsc. Sci.", 93, 241–245.
Derynck et al., "Cell" 38, 287–297, Aug. 1984.
Derynck et al., "Nature" 316, 701–705, Aug. 1985.
Jansen et al., "Nature", 306, 609–611, Dec. 1983.

Primary Examiner—Merrell C. Cashion, Jr.
Assistant Examiner—Suszn S. Rucker
Attorney, Agent, or Firm—Milton L. Honig

[57] ABSTRACT

A composition suitable for topical application to mammalian skin or hair comprises:
(a) a growth factor chosen from:
    (i) transforming growth factor alpha (TGF-$\alpha$),
    (ii) transforming growth factor beta (TGF-$\beta$),
    (iii) insulin-like growth factor-1 (IGF-1),
    (iv) fragments thereof of one or more of said growth factors, and
    (v) mixtures thereof of said growth factors or fragments of said growth factors; and
(b) a cosmetically acceptable vehicle for the growth factor or fragments thereof;

the total amount of growth factor being sufficient to increase hair growth in the rate, when the composition is applies topically thereto over a period of no more than 3 months, by at least 10% more than that obtainable using a control composition from which the said growth factor has been omitted, in accordance with the Rat Hair Growth Test.

18 Claims, No Drawings

COSMETIC COMPOSITION

FIELD OF THE INVENTION

The invention relates to a cosmetic or pharmaceutical composition for topical application to mammalian skin, the composition containing a hair growth promoter which is capable of promoting terminal hair growth, especially on the human scalp.

BACKGROUND

The Hair Bulb

The hair bulb is a compact, elongate structure, located in the dermis, and forms the lower most part of the hair follicle. The bulb is composed of three main cellular groups:

(i) a compact group of fibroblasts including a capillary system known as the dermal papilla;

(ii) surrounding epithelial tissue, a component of which proliferates and differentiates to give rise to the mature hair shaft, and (iii) a group of fibroblasts present around the outside of the bulb in the connective tissue sheath.

It is well recognized that the dermal papilla is essential for hair growth [Oliver R F (1970) J Embryol Exp Morphol 23, 219–236] and that, consequently, it is also essential for the proliferation of the adjacent epithelial cells which give rise to hair.

The Hair Growth Cycle

It should be explained that in most mammals, hair does not grow continuously, but undergoes a cycle of activity involving alternate periods of growth and rest. The hair growth cycle can be divided into three main stages, namely:

(i) the growth phase known as anagen, during which the hair follicle penetrates deep into the dermis with the cells of the bulb dividing rapidly and differentiating to form the hair, (ii) the transitional stage known as catagen, which is heralded by the cessation of mitosis, and during which the follicle regresses upwards through the dermis and hair growth ceases, (iii) the resting stage known as telogen, in which the regressed follicle contains a small secondary germ with an underlying ball of tightly packed dermal papilla cells.

The initiation of a new anagen phase is revealed by rapid proliferation of epithelial cells in the germ, expansion of the dermal papilla and elaboration of basement membrane components. The hair cycle is then repeated many times until, as a consequence of the onset of male pattern baldness, most of the hair follicles spend an increasing proportion of their time in the telogen stage, and the hairs produced become finer, shorter, and less visible; this is known as terminal to vellus transformation.

PRIOR ART

Alleged Baldness Cures

Although there have been many claims in the scientific literature to the promotion or maintenance of hair growth, by the topical application of hair tonics and the like, with the possible exception of minoxidil, none has ever proved to be effective or to be sufficiently free from disadvantageous clinical side effects, whether administered topically, orally or systemically, to warrant commercial exploitation as an ethical pharmaceutical, proprietary medicine, or as a cosmetic product. Possibly, the only means which has met with partial success for growing hair on the bald or balding human head is transplantation of hair to the bald areas. This is, however, a painful operation and is not always successful. Furthermore, it is immediately apparent to the casual observer that the subject has received a hair transplant and it may take many months or even years before hair regrowth, following this operation, assumes an appearance which resembles that of naturally growing hair.

Among the many hair regrowth studies that have been reported in the literature, there is included the work of Bazzano as described in PCT International Publication No. WO 85/04577. This publication describes a composition which is useful for increasing the rates of hair growth on mammalian skin, prolonging the anagen phase of the hair growth cycle and for treating various types of alopecias. The composition in question contains a pyrimidine carbamate.

It has also been reported in U.S. Pat. No. 4,139,619 to Chidsey assigned to the Upjohn Company, that a topical composition comprising minoxidil as the free base or acid addition salt thereof, or certain specified related iminopyrimidines, is useful in stimulating the conversion of vellus hair to growth as terminal hair, as well as increasing the rate of growth of terminal hair.

In spite of the apparent stimulation of hair growth or regrowth in a small percentage of patients reported independently by Bazzano and Chidsey, there is some concern that systemic side-effects can result, particularly following topical application of minoxidil. Thus it is generally recognized in the medical literature that the side effects of orally administered minoxidil are very serious, and include fluid retention, tachycardia, dyspnea, gynecomastia, fatigue, nausea and cardiotoxicity.

It has also been proposed in DE-A-3 431 266 (Birzer) to administer externally or internally hair bulb cells with the papilla from slaughtered animals in order to stimulate growth and genesis of hair and to counteract hair loss and hair graying. The cells are obtained from the hide of animals and can be applied internally by injection or as tablets or drops, and externally as shampoos, creams and soaps.

The isolation of dermal papillae from human hair follicles has been reported by Messenger, A. G., British Journal of Dermatology (1984), 110, 685–689. Messenger has established primary cell cultures from the papilla explants in a nutrient medium.

In addition to the alleged benefits of employing the pyrimidine carbamates of Bazzano or minoxidil of Upjohn, many other hair regrowth studies have been reported in the literature. In particular, the work of Meyer et al (1961) in the Proceedings of the Society of Experimental and Biological Medicine, 108, 59–61, is worthy of mention. Meyer and his co-workers repeatedly injected acid mucopolysaccharides into the skin of shaved rabbits and reported observing the initiation of the hair growth cycle with stimulation of hair growth which in some instances appeared to be thicker than usual. They found that heparan sulphate was particularly active, while dermatan sulphate and chondroitin-6-sulphate were also active in this respect, but to a lesser extent.

It has also been reported by Frajdenrajch in EP-A-0 035 919 to include chondroitin sulphate in a hair composition in order to prevent loss and encourage growth of the hair.

Also, Shansho Seigaku in JA-59/186911 describes a shampoo containing a mucopolysaccharide such as chondroitin sulphate.

There are also other references, mainly of Japanese origin, which claim the use of chondroitin sulphate in preparations for topical application to human skin, particularly as hair tonics.

BACKGROUND TO THE INVENTION

The reported role of the dermal papilla which is situated at the base of the hair follicle, and the closely related cells of the connective tissue sheath which surrounds the hair follicle are alleged to be of key importance in governing the cyclic behavior of hair follicles. This has been shown, for example, directly by Oliver R F (1970) J Embryol Exp Morphol., 23, 219-236, and the changes in the dermal papilla during the hair cycle are consistent with these observations. At the end of anagen, there is a sudden loss of fibronectin [Couchman J R and Gibson W T, (1985) Dev Biol., 108, 290-298] and metachromatic (glycosaminoglycan) staining [Montagna W et al, (1952) Q J Microsc Sci., 93, 241-245] from the connective tissue matrix of the dermal papilla which then undergoes condensation.

Conversely, expansion and elaboration of new matrix is associated with the onset of anagen. A direct role of matrix components in stimulating hair growth was suggested by the work of Meyer et al (1961), [supra].

It is accordingly apparent that glycosaminoglycan breakdown is an important early change in catagen, and since there is already evidence for a link between the presence of intact glycosaminoglycans and hair growth, we have suggested that prevention of glycosaminoglycan breakdown may lead to earlier onset and/or prolongation of anagen. This would effectively retard hair loss and reverse baldness.

Experience has shown that it is difficult to harvest a substantial quantity of dermal papilla cells, either by dissection or by the enzymic treatment of animal hides advocated by Birzer [supra]. Furthermore, it has been discovered that the dermal papilla cells obtained from animals are not effective in promoting hair growth in the human subject, and that ideally, human dermal papilla cells should be employed for this purpose. Accordingly, cells derived from one host (e.g. cow) are immunologically distinct from any other species (e.g. man), and therefore, it is not surprising that upon injection, they are rejected by the new host's immune system and destroyed.

Accordingly, if it is desired to promote hair growth in other mammals using animal cells, then ideally dermal papilla cells derived from the corresponding species of mammal should be employed.

Having regard to the fact that man has sought ways and means for promoting hair growth or regrowth in the bald or balding human subject since time immemorial, without discovering a totally safe, feasible and satisfactory treatment for promoting hair growth, it is all the more surprising that a means has now been discovered for generating hair growth factors from mammalian dermal papilla cells.

Essentially, we have been able to isolate hair follicles from skin and culture dermal papilla cells derived therefrom in a nutrient medium to obtain enhanced numbers of cells. Culture supernatants, have been harvested from cultured human dermal papilla cells, and after concentration, quantities of specific growth factors have been isolated and identified. When these identified growth factors are applied topically to bald or balding human scalps in a sufficient amount, they have been shown to promote, maintain or increase hair growth or regrowth.

DEFINITION OF THE INVENTION

Accordingly, the invention provides a composition suitable for topical application to mammalian skin or hair, which comprises:
(a) a growth factor chosen from:
(i) transforming growth factor alpha (TGF-α),
(ii) transforming growth factor beta (TGF-β),
(iii) insulin-like growth factor-1 (IGF-1),
(iv) fragments thereof of one or more of said growth factors, and
(v) mixtures thereof of said growth factors or fragments of said growth factors;
(b) a cosmetically acceptable vehicle for the growth factor or fragments thereof;
the amount of growth factor being sufficient to increase hair growth in the rat, when applied topically thereto over a period of no more than 3 months, by at least 10% more than that obtainable using a control composition from which the said growth factor has been omitted, in accordance with the Rat Hair Growth Test.

DISCLOSURE OF THE INVENTION

The Growth Factor

The composition according to the invention comprises a growth factor chosen from:
(i) transforming growth factor-α(TGF-α),
(ii) transforming growth factor-β(TGF-β),
(iii) insulin-like growth factor 1 (IGF 1), and
mixtures thereof, in an amount sufficient to increase hair growth in the rat, when applied thereto, by at least 10% more than that obtainable using a control composition from which said growth factor has been omitted.

Transforming Growth Factor-α is the subject of the paper by Derynck et al, in Cell 38 287-297, August 1984 entitled "Human Transforming Growth Factor -α : Precursor Structure and Expression in *E. coli*". In this paper, which is hereby incorporated by reference, it is stated that TGF-α is secreted by many human tumors and can induce the reversible transformation of non nontransformed cell lines. TGF-α in its mature form is a protein comprising fifty amino acid residues and its amino acid sequence is given in FIG. 4 on page 289 of the above paper. TGF-α protein has also been found in some tissues during normal embryonic development, and in epidermis.

TGF-α has not previously been isolated from the dermal papilla nor has its role in inducing, maintaining or increasing hair growth been reported. TGF-α is available commercially and can be prepared using classical peptide synthesis, or by recombinant DNA technology.

Transforming growth factor-β is the subject of a paper by Derynck et al in Nature 316 701-705, August 1985 entitled "Human Transforming Growth Factor -β Complementary DNA Sequence and Expression in Normal and Transformed Cells". In this paper, which is hereby incorporated by reference, it is stated that TGF-β has been isolated from tumor and normal cells and tissues including kidney, placenta and blood platelets. TGF-β in its mature form is a protein comprising 112 amino acid residues and its amino acid sequence is given in FIG. 1 on page 702 of this paper. TGF-β has not previously been isolated from the dermal papilla, nor has its role in inducing, maintaining or increasing hair growth been reported. TGF-β is available commercially and is usually purified from human or porcine platelets.

Insulin-like growth factor-1 (IGF-1) is the subject of a paper by Jansen et al, in Nature, 306 609–611, December 1983 entitled "Sequence of cDNA Encoding Human Insulin-like Growth Factor I Precursor". In this paper, which is hereby incorporated by reference, it is stated that IGF-1 has been isolated from the liver. IGF-1 in its mature form is a protein comprising 70 amino acid residues, and its amino acid sequence is given in FIG. 2 on page 610 of this paper.

It has been reported that IGF-1 is manufactured by the dermal papilla, but its role in inducing, maintaining or increasing hair growth has not been reported. IGF-1 is available commercially and can be prepared using classical peptide synthesis, purified from human serum or manufactured by recombinant DNA technology.

The amount of growth factor to be incorporated with a suitable vehicle into compositions for topical use can vary widely, but in general, an amount of from 0.0002 to 10 mg/ml is suitable. Preferred concentrations of each of the growth factors are:

for TGF-α: from 0.0005 to 30 μg/ml, preferably from 5 to 300 ng/ml for TGF-β: from 0.0002 to 20 μg/ml, preferably from 0.2 to 200 ng/ml for IGF-1 : from 0.0002 to 70 μg/ml, preferably from 2 to 700 ng/ml It is possible to employ any one of the three growth factors, or a combination of any two or, indeed, all three growth factors in composition according to the invention.

The Vehicle

The composition according to the invention also comprises a solid, semi-solid or liquid cosmetically and-/or physiologically acceptable vehicle, to enable the hair growth factor substance to be conveyed to the skin at an appropriate dilution. The nature of the vehicle will depend upon the method chosen for topical administration of the composition. The vehicle can itself be inert or it can possess physiological or pharmaceutical benefits of its own.

The selection of a vehicle for this purpose presents a wide range of possibilities depending on the required product form of the composition. Suitable vehicles can be classified as described hereinafter.

It should be explained that vehicles are substances which can act as diluents, dispersants, or solvents for the hair growth factor which therefore ensure that it can be applied to and distributed evenly over the hair and/or scalp at an appropriate concentration. The vehicle is preferably one which can aid penetration of the hair growth factor into the skin to reach the immediate environment of the hair follicle. Compositions according to this invention can include water as a vehicle, and/or at least one cosmetically acceptable vehicle other than water.

Vehicles other than water that can be used in compositions according to the invention can include solids or liquids such as emollients, solvents, humectants, thickeners and powders. Examples of each of these types of vehicles, which can be used singly or as mixtures of one or more vehicles, are as follows:

Emollients, such as stearyl alcohol, glyceryl monoricinoleate, glyceryl monostearate, propane-1,2-diol, butane-1,3-diol, mink oil, cetyl alcohol, ispropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, dimethylpolysiloxane, di-n-butyl sebacate, isopropyl myristate, isopropyl palmitate, isopropyl stearate, butyl stearate, polythylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, acetone, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate.

Activity Enhancer

The composition according to the invention also preferably comprises a means for enhancing the activity of the hair growth factors, especially to enhance their penetration through the skin following topical application, with the consequence that hair growth can be promoted.

The vehicle present in the composition according to the invention preferably functions as or comprises an activity enhancer which can be chosen from a wide variety of molecules capable of functioning in different ways to enhance the benefit of the hair growth factors. Particular classes of activity enhancers include other hair growth stimulants, protein stabilizing agents and penetration enhancers and cationic polymers, whose presence can further improve the delivery of the hair growth factor through the stratum corneum to the immediate environment of the hair follicle.

Some activity enhancers can also function as vehicles for the hair growth factors.

The means for enhancing the activity of the hair growth factors can also take the form of an iontophoretic device as will be explained later. This and other means for enhancing the activity of the said growth factors are now disclosed in greater detail.

(a) Other Hair Growth Stimulants

Examples of other substances which themselves possess the ability to stimulate or increase the rate of terminal hair growth include, for example;
Benzalkonium chloride
Benzethonium chloride Phenol
Estradiol
Diphenhydramine hydrochloride
Chlorpheniramine maleate
Chlorophyllin derivatives
Cholesterol
Salicylic acid
Cystine
Red pepper tincture
Benzyl nicotinate
dl-Menthol
Peppermint oil
Calcium pantothenate
Panthenol
Castor oil
Hinokitiol
Prednisolone
Resorcinol, and
Retinoids, or pharmaceutically acceptable esters, ethers or salts thereof.

Further substances which themselves possess the ability to increase the rate of terminal hair growth (i) α-1,4 esterified disaccharides described by Choay S. A. in EP-A-0 064 012, having the structure (1):

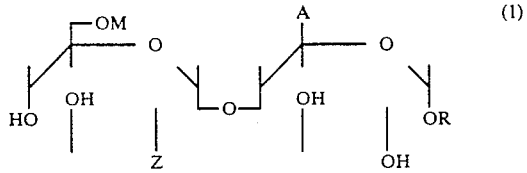

where

Z represents a functional nitrogen group, such as an azide or a group having the structure —NHB, in which B represents —H or a functional group such as acetyl or sulphate as a salt with an organic or mineral cation;

M represents —H or $SO_3M_1$, where $M_1$ is an organic or metallic cation, particularly an alkali metal; or an acetyl group;

R represents a $C_1$ to $C_4$ alkyl radical, especially methyl; or an aryl radical;

A represents a functional group such as an acid —$COOR_1$, where $R_1$ represents —H or a $C_1$ to $C_4$ alkyl radical, especially methyl; or a metal, especially an alkali metal;

(ii) esterified oligosaccharides as described by Unilever in EP-A-0 211 610 including at least one esterified disaccharide unit consisting of a uronic acid residue having the structure (2):

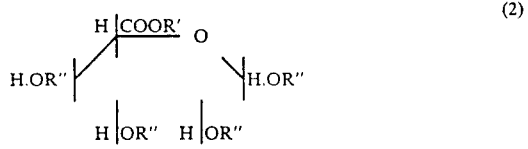

and a hexosamine residue having the structure(3):

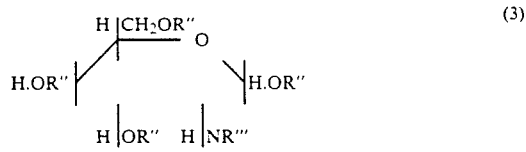

where

R' is $C_3$ to $C_{10}$ alkyl or

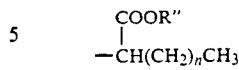

R" is —H, $C_1$ to $C_4$ alkyl, —$CO(CH_2)_mCH_3$, —$SO_3M'$,

R'" is —H, —$CO(CH_2)_mCH_3$, or —$SO_3M'$,

M' is —H, or a metallic or organic cation n is 0 or an integer of from 1 to 7, and m is 0 or the integer 1 or 2;

the groups designated R" being the same or different, one R" group from each pyranose ring structure being linked by a glycosidic linkage having the configuration α-1,3, α-1,4, β-1,3 or β-1,4; and the —COOR', —CH$_2$OR" and —OR" groups being of either configuration with respect to the pyranose rings;

(iii) Minoxidil and its derivatives, as described by the Upjohn Co, in GB 1 167 735, (iv) Minoxidil glucuronide, as described by Unilever in EP-0 242 967

(v) Minoxidil sulphates, as described by the Upjohn Co., in WO 86/04231.

(vi) Direct proteoglycanase inhibitors, such as 1,10-phenanthroline.

(vii) Glycosaminoglycanase inhibitors, such as aldonolactones and esterified aldonolactones having the structure (5):

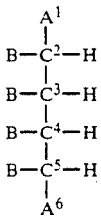

where $A^1$ and $A^6$ are —H,

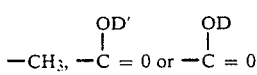

B is OD" or a lactone linkage to position 1 or 6, or —NHCOCH$_3$ and where D is —H or $C_2$ to $C_8$ alkyl, D' is the remainder of the molecule joined through another C atom at positions 2 to 5 to form a lactone, D" is —H or $C_2$ acyl (ie acetyl) to $C_4$ of either configuration with respect to the backbone of this molecule; preferred examples of which include:

L-Galactono-1,4-lactone
L-Arabino-1,5-lactone
D-Fucono-1,5-lactone
D-Glucaro-1,4-lactone
D-Glucurono-6,3-lactone
Galactaric acid lactone
2-Acetamido-2-deoxygluconolactone
2-Acetamido-2-deoxygalactono-lactone
D-Glucaro-1,4:6,3-dilactone
L-Idaro-1,4-lactone
2,3,5-Tri-0-acetyl-D-glucaro-1,4-lactone
2,5-Di-0-acetyl-D-glucaro-1,4:6,3-dilactone (viii) Glycosaminoglycanase inhibitors, such as monosaccharides and esterified monosaccharides having the structure (6):

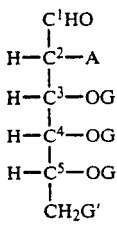
(6)

where
A is —OG or —NHCOCH$_3$
G is —H, —SO$_3$M'', C$_2$ (ie acetyl) to C$_4$ acyl
G' is —H or —OG
M'' is —H or a metal cation
wherein the functional groups can be in either configuration with respect to the backbone of the above molecule;
preferred examples of which include:
N-Acetylglucosamine
N-Acetylgalactosamine
D-Galactosamine
D-Glucosamine-3-sulphate
N-Acetylmannosamine (ix) glycosaminoglycan chain cellular uptake inhibitors such as, hexuronic acid and esters thereof which may be represented by the generic structure (7):

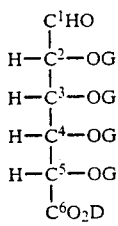
(7)

where
G is —H, —SO$_3$M'', C$_2$ (ie acetyl) to C$_4$ acyl;
D is —H or C$_2$ to C$_8$ alkyl
M'' is —H or a metal cation;
wherein the functional groups can be in either configuration with respect to the backbone of the above molecule;

(x) Chemical inhibitors of glycosidase activity chosen from lactams having the structure (8):

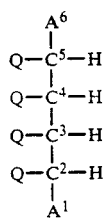
(8)

where
A$^1$ and A$^6$ are —H, —CH$_3$

—CH$_2$OT

or 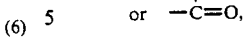,

A$^1$ and A$^6$ being the same or different, and at least one of which being the group:

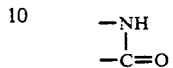

in a lactam ring;
and where Q is —OT', —NHT' or a lactam linkage to A$^1$ or A$^6$;
the Q groups being the same or different, and at least one of which is involved in a lactam linkage;
and where T is the same or different and is chosen from —H, —C$_p$H$_{2p+1}$ or a metal ion,
T' is —H or —COC$_p$H$_{2p+1}$, and
p is an integer of from 1 to 22;
provided that:
where any of the Q groups is —OT' or —NHT', then that group or groups can be of either stereochemical configuration with respect to the plane of the ring,
preferred examples of which include:
D-glucaro-1,5-lactam
L-Galactono-1,4-lactam,
L-Arabino-1,5-lactam,
D-Fucono-1,5-lactam,
D-Glucaro-1,4-lactam,
D-Glucurono-6,3-lactam,
1,2,5-tri-0-acetyl-D-glucurono-6,3-lactam
2-Acetamido-2-deoxygluconolactam,
2-Acetamido-2-deoxygalactonolactam,
D-Glucaro-1,4:6,3-dilactam,
L-Idaro-1,4-lactam,
2,3,5-Tri-0-acetyl-D-glucaro-1,4-lactam,
2,5-Di-0-acetyl-D-Glucaro-1,4:6,3-dilactam,
D-glucaro-1,5-lactam ethyl ester;

(xi) chemical activators of protein kinase C enzymes chosen from diacylglycerols having the structure (9):

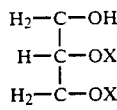
(9)

where X is the same or different and is represented by the grouping:

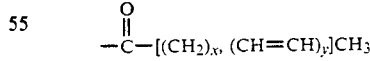
(9a)

where
x is O or an integer of from 1 to 28, and
y is 0 or an integer of from 1 to 5;
the OX groups being of either stereochemical configuration with respect to the carbon backbone of the glycerol molecule, the double bonds being of either cis or trans configuration;
preferred examples of which include:
1,2-Dibutanoyl-rac-glycerol
1,2-Dihexanoyl-sn-glycerol
1,2-Dioctanoyl-rac-glycerol 1,2-Dioctanoyl-sn-glycerol
1,2-Didecanoyl-rac-glycerol
1-Oleoyl-2-acetyl-rac-glycerol
1-Oleoyl-2-acetyl-sn-glycerol
1-Stearoyl-2-arachidonoyl-sn-glycerol
1,2-Distearoyl-rac-glycerol
1,2-Dipentadecanoyl-sn-glycerol
1,2-dipentadecanoyl-rac-glycerol
1,2-Dipalmitoyl-rac-glycerol
1,2-Dipalmitoyl-sn-glycerol
1,2-Diseptadecanoyl-rac-glycerol
1,2-Dioleoyl-sn-glycerol
1,2-Dioleoyl-rac-glycerol
1,2-Diarachidonoyl-sn-glycerol
1,2-Dieicosanoyl-sn-glycerol
1,2-Didoeicosanoyl-rac-glycerol, and
1,2-Dioctaeicosanoyl-sn-glycerol.

(b) Protein Stabilizing Agents

As has been stated earlier, the hair growth factor comprises one or more proteins, and therefore its benefit in promoting hair growth can be maintained or improved by including a protein stabilizing agent in the composition according to the invention. As an example of this effect, it is to be noted that the skin contains natural proteases which might at least partially degrade the hair growth factor. Therefore, the presence of protein stabilizing agent such as a proteinase inhibitor or a secondary protein for which with the hair growth factor, the natural skin proteinase will compete, can protect the hair growth factor until it reaches the immediate environment of the hair bulb.

Examples of protein stabilizing agents accordingly include:
Glycerol
Ethylenediaminetetraacetic acid
Cysteine
$\alpha_2$-Macroglobulin
Serum, and
other proteinase inhibitors.

(c) Penetration Enhancers

As has been stated earlier, the presence of a penetration enhancer can potentiate the benefit of the hair growth factor by improving its delivery through the stratum corneum to its site of action in the immediate environment of the hair follicle close to the dermal papilla.

The penetration enhancer can accordingly function in a variety of ways. It can for example, improve the distribution of the hair growth factor on the skin surface or, it can increase its partition into the skin from the composition when applied topically, so aiding its passage to its site of action. Other mechanisms enhancing the benefit of the hair growth factor may also be involved.

Examples of penetration enhancers accordingly include certain non-electrolytes, such as:
2-methyl propan-2-ol
Propan-2-ol
Ethyl-2-hydroxypropanoate
Hexan-2,5-diol
POE(2) ethyl ether
Di(2-hydroxypropyl) ether
Pentan-2,4-diol
Acetone
POE(2) methyl ether
2-hydroxypropionic acid
Propan-1-ol
1,4 Dioxane
Tetrahydrofuran
Butan-1,4-diol Other penetration enhancers whose presence in the composition according to the invention can further improve the delivery through the stratum corneum include certain esters, such as:
Propylene glycol dipelargonare
Polyoxypropylene 15 stearyl ether
Octyl alcohol
POE ester of oleyl alcohol
Oleyl alcohol
Lauryl alcohol
Dioctyl adipate
Dicapryl adipate
Diisopropyl adipate
Diisopropyl sebacate
Dibutyl sebacate
Diethyl sebacate
Dimethyl sebacate
Dioctyl sebacate
Dibenzyl sebacate
Dibutyl suberate
Dioctyl azelate
Dibutyl azelate
Dimethyl azelate
Dibutyl succinate
Dibutyl phthalate
Didecyl phthalate
Ethyl myristate
Butyl myristate
Isopropyl palmitate
Ethyl laurate
Decyl oleate
2-ethyl-hexyl pelargonate
Isopropyl isostearate
Butyllaurate
Benzyl benzoate
Butyl benzoate
Hexyl laurate
Ethyl caprate
Ethyl caprylate
Ethyl caproate
Butyl stearate
Benzyl salicylate, and
Ethyl salicylate Yet further penetration enhancers include esters of pyroglutamic acid having the structure (10):

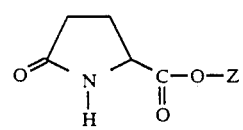

(10)

or

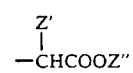

where
Z is $C_1$ to $C_{30}$ alkyl,
and where
Z' and Z'' are the same or different and are each represented by H or the grouping (11):

$[(CH_3)_u, (CH_2OH)_v, (CH_2)_w, (CH_3CH_2)_s, (CH=CH)_z]$- (11)

where u is zero or 1
v is zero, or the integer 1 or 2,
w is zero, or an integer of from 1 to 21
s is zero, or an integer of from 1 to 4,
y is zero, or the integer 1 or 2,
z is zero, or an integer of from 1 to 22, and
$u + v + w + x + y + z$ is an integer of from 1 to 22;
provided that when the subgrouping (CH=CH) is present, then the total number of carbon atoms in said grouping is from 10 to 22.

Examples of suitable esters of pyroglutamic acid where R in structure (10) is $C_1$ to $C_{30}$ alkyl are:
pyroglutamic acid methyl ester
pyroglutamic acid ethyl ester
pyroglutamic acid n-propyl ester
pyroglutamic acid n-butyl ester
pyroglutamic acid n-heptyl ester
pyroglutamic acid n-octyl ester
pyroglutamic acid n-nonyl ester
pyroglutamic acid n-decyl ester
pyroglutamic acid n-undecyl ester
pyroglutamic acid n-dodecyl ester
pyroglutamic acid n-tridecyl ester
pyroglutamic acid n-tetradecyl ester
pyroglutamic acid n-hexadecyl ester
pyroglutamic acid n-octadecyl ester
pyroglutamic acid n-eicosyl ester
pyroglutamic acid iso-propyl ester
pyroglutamic acid 2-methylhexyl ester
pyroglutamic acid 2-ethylhexyl ester
pyroglutamic acid 3,7-dimethyloctyl ester
pyroglutamic acid 2-hexyldecyl ester
pyroglutamic acid 2-octyldodecyl ester
pyroglutamic acid 2,4,4-trimetyl-1-pentane ester
pyroglutamic acid methyloctyl ester Particularly preferred esters of this group are those where Z in structure (10) is $C_1$ to $C_{14}$ alkyl, (linear or branched), especially $C_1$ to $C_6$ (linear or branched).

Further examples of preferred esters of pyroglutamic acid, where Z in structure (10) is

are those where Z' and/or Z" having the structure shown for grouping (11), include straight and branched chain, saturated or unsaturated aliphatic groups having from 1 to 22 carbon atoms, such as the alkyl groups:
methyl
ethyl
propyl
iso-propyl
butyl
iso-butyl
n-valeryl
iso-valeryl
n-caproyl
n-heptyl
n-caprylyl
n-capryl
lauryl
myristyl
palmityl
stearyl, and
arachidyl.
and the $C_{10-22}$ alkenyl groups:
linoleyl
linolenyl
γ-linolenyl
arachidonyl, and
columbinyl.

Further examples of the grouping (11) also include hydroxyalkyl groups having from 1 to 22 carbon atoms, such as:
hydroxymethyl
2-hydroxyethyl
2-hydroxy-n-propyl
3-hydroxy-n-propyl
2-hydroxy-n-butyl
3-hydroxy-n-butyl
4-hydroxy-n-butyl
5-hydroxy-n-valeryl
6-hydroxy-n-caproyl
2,3-dihydroxy-n-propyl
2,3-dihydroxy-n-butyl
12-hydroxystearyl.

It is to be understood that the above list is not exhaustive, there being many other examples of alkyl or substituted alkyl groups expressed by the above generic grouping (11).

Further specific examples of esters of pyroglutamic acid which are particularly suited to use as penetration enhancers are:
2-[pyroglutamoyloxy]-propionic acid
methyl-2-[pyroglutamoyloxy]-acetate
ethyl-2-[pyroglutamoyloxy]-n-propionate
ethyl-2-[pyroglutamoyloxy]-n-butyrate
ethyl-2-[pyroglutamoyloxy]-iso-butyrate
ethyl-2-[pyroglutamoyloxy]-n-valerate
ethyl-2-[pyroglutamoyloxy]-n-caproate
ethyl-2-[pyroglutamoyloxy]-n-heptylate
ethyl-2-[pyroglutamoyloxy]-n-caprylate
ethyl-2-[pyroglutamoyloxy]-n-pelargonate
ethyl-2-[pyroglutamoyloxy]-3-hydroxybutyrate
iso-propyl-2-[pyroglutamoyloxy]-n-propionate
iso-propyl-2-[pyroglutamoyloxy]-n-caprylate
n-propyl-2-[pyroglutamoyloxy]-n-propionate
n-propyl-2-[pyroglutamoyloxy]-n-caprylate
stearyl-2-[pyroglutamoyloxy]-n-propionate
12-hydroxystearyl-2-[pyroglutamoyloxy]-n-propionate
stearyl-2-[pyroglutamoyloxy]-n-stearate
palmityl-2-[pyroglutamoyloxy]-n-propionate
linoleyl-2-[pyroglutamoyloxy]-n-propionate
linoleyl-2-[pyroglutamoyloxy]-n-caprylate
lauryl-2-[pyroglutamoyloxy]-n-caprylate
stearyl-2-[pyroglutamoyloxy]-n-caprylate
glyceryl mono(2-[pyroglutamoyloxy]-n-caprylate)
glyceryl mono(2-[pyroglutamoyloxy]-n-caprylate), and
glyceryl di(2-[pyroglutamoyloxy]-n-propionate).

It is to be understood that the above lists of specific examples of esters of pyroglutamic acid are not exhaustive, there being many other examples expressed by the generic structure of these esters.

Further examples of penetration enhancers include:
glyceryl mono(2-[pyroglutamoyloxy]-n-caprylate), and
Dimethyl sulphoxide
N,N-Dimethyl acetamide
N,N-Dimethyl formamide
2-Pyrrolidone
1-Methyl-2-pyrrolidone
5-Methyl-2-pyrrolidone
1,5-Dimethyl-2-pyrrolidone
1-Ethyl-2-pyrrolidone
Phosphine oxides
Sugar esters Tetrahydrofurfural alcohol
Urea
Diethyl-m-toluamide, and
1-Dodecylazacyloheptan-2-one (d) Wetting Agents Further examples of penetration enhancers include wetting agents, by which term is meant a surface active agent which, when added to water, causes it to penetrate more easily into or spread on the surface of another material, by reducing the surface tension of water at the water-air interface; The Condensed Chemical Dictionary, Eighth Edition 1971, pg 937].

By "surface active agent" is meant, any compound that reduces surface tension when dissolved in water or water solutions; [The Condensed Chemical Dictionary, Eighth Edition 1971, pg 840].

By "surface tension", is meant the inward force of the liquid, due to the attraction of the molecules below the surface. This force varies from one liquid to another, that of water being high compared with that of alcohol, for example; [The Condensed Chemical Dictionary, Eighth Edition 1971 pg 841].

The function of the wetting agent in the composition according to the invention is accordingly to enable the growth factor to be dispersed readily on the skin's surface or on the hair, and to facilitate its penetration into the skin to the region of the hair bulb and the associated dermal papilla cells.

The selection of a wetting agent for this purpose presents a wide range of possibilities known in the art.

Particularly preferred examples of wetting agents include the following surface active agents.

(i)

Anionic surface active agents, such as metallic or alkanolamine salts of fatty acids for example sodium laurate and triethanolamine oleate;
alkyl benzene sulphones, for example triethanolamine dodecyl benzene sulphonate;
alkyl sulphates, for example sodium lauryl sulphate;
alkyl ether sulphates, for example sodium lauryl ether sulphate [2 to 8 EO];
sulphosuccinates, for example sodium dioctyl sulphonsuccinate;
monoglyceride sulphates, for example sodium glyceryl, monostearate monosulphate;
isethionates, for example sodium isethionate;
methyl taurides, for example Igepon T;
acylsarcosinates, for example sodium myristyl sarcosinate;
acyl peptides, for example Maypons and Lamepons;
acyl lactylates,
polyalkoxylated ether glycollates, for example trideceth-7 carboxylic acid;
phosphates, for example sodium dilauryl phosphate.

(ii)

Cationic surface active agents, such as amine salts, for example sapamin hydrochloride;
quartenary ammonium salts, for example Quaternium 5, Quaternium 31 and Quaternium 18;

(iii)

Amphoteric surface active agents, such as imidazol compounds, for example Miranol;
N-alkyl amino acids, such as sodium cocaminopropionate and asparagine derivatives;
betaines, for example cocamidopropylebetaine (iv)

Nonionic surface active agents, such as fatty acid alkanolamides, for example oleic ethanolamide;
esters of polyalcohols, for example Span; polyglycerol esters, for example that esterified with $C_{12-18}$ fatty acids and one or several OH groups;
polyalkoxylated derivatives, for example polyoxy:-polyoxyethylene stearate;
ethers, for example, polyoxyether lauryl ether;
ester ethers, for example Tween;
amine oxides, for example coconut and dodecyl dimethyl amine oxides.

Mixtures of two or more of the above surface active agents can be employed as wetting agents in the composition according to the invention.

(e) Cationic Polymers

Certain cationic polymers also function as activity enhancers. Particularly preferred cationic polymers for this purpose are chosen from:
Guar Hydroxypropyltrimonium chloride
Quaternium-19
Quaternium-23
Quaternium-40
Quaternium-57
Poly(dipropyldiallylammonium chloride)
Poly(methyl-$\beta$-propaniodiallyl ammonium chloride)
Poly(diallylpiperidinium chloride)
Poly(vinyl pyridinium chloride)
Quaternized poly (vinyl alcohol)
Quaternized poly (dimethylaminoethylmethacrylate); and mixtures thereof.

The amount of vehicle in the composition, including water if present, should preferably be sufficient to carry at least a portion of a selected hair growth factor to the skin in an amount which is which is sufficient effectively to enhance hair growth. The amount of the vehicle can comprise the balance of the composition, particularly where little or no other ingredients are present in the composition. Accordingly, the vehicle or vehicles can comprise from 1 to 99.9999%, preferably from 50 to 99.5% and ideally from 90 to 99% by weight of the compositions.

When the vehicle is an activity enhancer, the amount present when employed in accordance with the invention, will normally be from 0.1 to 50%, preferably from 0.5 to 25% and most preferably from 0.5 to 10% by weight of the composition.

(f) Iontophoresis

A further means for enhancing the activity of the hair growth factors following topical application is the use of iontophoresis. A preferred iontophoretic device for this purpose comprises a pad of absorbent material, such as a nonwoven sheet or sponge, impregnated with a solution containing the growth factors, as herein defined, the pad carrying an electrode, for example in the form of a metallic sheet, through which an electric current can be passed, in order to enhance delivery of the growth factors to and through the epidermal layer of the skin.

Perfume

The composition according to the invention can also optionally comprise a perfume in an amount sufficient to make the composition acceptable to the consumer and pleasant to use. Usually, the perfume will form from 0.01 to 10% by weight of the composition.

Preservation of the Composition

The composition according to the invention is preferably preserved in such a manner that it will enjoy an extended shelf life following manufacture and prior to sale and use. Ideally the composition will have an indefinite shelf life.

It is accordingly apparent that the hair growth factor is likely to be prone to attack by bacteria, molds and fungi and other microbial influences, particularly at pH values near neutrality that characterize the preferred composition. The shelf-life of the composition can therefore be unacceptably short due to the biodegradation of the growth factor unless steps are taken to preserve the composition.

In order to be preserved, the composition should preferably be free, or substantially free, from viable microbial contaminants that are capable of resulting in microbial spoilage of the composition, and/or biodegradation of the growth factor prior to topical application of the composition to mammalian skin or hair. It is to be understood, however, that the invention is also concerned with compositions, as herein defined, which may contain viable but dormant microorganisms, such as bacterial spores, provided that the conditions of preservation do not result in substantial proliferation of the microorganisms prior to use of the composition.

Examples of methods that can be employed to achieve preservation of the composition, includes the following:

(i) Serialization

The composition according to the invention can be preserved by serialization to remove or kill substantially all viable microbial contaminants. This can be achieved for example by irradiation using a lethal dose of gamma rays, by heat serialization or by ultrafiltration using techniques that are well established in the pharmaceutical industry.

(ii) Extreme of pH value

The composition according to the invention can alternatively be preserved by adjusting its pH to a value that is either too low (e.g. pH <2) or too high (e.g. pH >12) to permit significant proliferation of microbial contaminants. The pH of the composition can accordingly be adjusted to desired high or low values by addition of an alkali or acid as a pH adjustant.

(iii) Chemical Preservative

The composition according to the invention can also be preserved by including in it a chemical preservative which functions to prevent the growth of or kill bacteria, fungi or other microorganisms.

Examples of chemical preservatives include ethanol, benzoic acid, sodium benzoate, sorbic acid, potassium sorbate, sodium propionate and the methyl, ethyl, propyl and butyl esters of p-hydroxybenzoic acid. The amount of chemical preservative that can be incorporated in the composition according to the invention will generally be from 0.05 to 5%, preferably from 0.1 to 2% by weight, the amount chosen being sufficient to arrest microbial proliferation.

(iv) Water activity depressants

The composition according to the invention can also be preserved by the inclusion of a water activity depressant such as glycerol, propylene glycol, sorbitol, sugars and salts, for examples alkali metal halides, sulphates and carboxylates. When employing a water activity depressant, sufficient should be incorporated in the composition according to the invention to reduce the water activity ($a_w$) from 1 to <0.9, preferably to <0.85 and most preferably <0.8, the lowest of these values being that at which yeasts, molds and fungi will not proliferate.

Other ingredients

The composition according to the invention can contain ingredients other than those already mentioned, depending on the form of the intended product. It is, for example, possible to include antiseptics, antioxidants, emulsifiers, coloring agents, detergents and antiinflammatory agents, such as steroidal (e.g., corticosteroids) and non-steroidal (e.g., ibuprofen and its derivatives) compounds.

The composition according to the invention can also be employed as a vehicle for a wide variety of cosmetically or pharmaceutically active ingredients, particularly ingredients which have some beneficial effect when applied to the skin other than the promotion of hair growth.

Process

The invention also provides a process for the preparation of a composition suitable for topical application to the hair and/or scalp which comprises the step of preparing a composition comprising one or more of the said growth factors together with a cosmetically acceptable vehicle.

Product Form

The composition of the invention can be formulated as a liquid, for example as a lotion, shampoo, conditioner or milk for use in conjunction with an applicator such as a roll-ball applicator, or a spray device such as an aerosol can containing propellant, or a container fitted with a pump to dispense the liquid product.

When the composition is contained in a pressurized aerosol container, the propellant in providing an inert headspace within the container will aid in preserving the composition.

The composition of the invention can also be solid or semi-solid, for example a stick, cream or gel, for use in conjunction with a suitable applicator or simply a tube, bottle or lidded jar, or as a liquid-impregnated fabric, such as a tissue wipe.

The invention accordingly also provides a closed container containing a composition as herein defined.

Use of the Growth Factor for Inducing, Maintaining or Increasing Hair Growth

The invention also provides for the use of the growth factor, as herein defined, for topical application to mammalian hair or skin particularly the scalp, for inducing, maintaining or increasing terminal hair growth, and/or converting vellus hair to growth as terminal hair.

The composition of the invention is accordingly primarily intended for topical application to the scalp of the human subject, particularly where the head is already bald or balding, in order to reduce or prevent the onset of baldness.

The invention also provides for the use of the growth factor in the preparation of a therapeutic composition for treating baldness.

The amount of the composition and the frequency of application to the hair and/or scalp can vary widely, depending on personal needs, but it is suggested as an example that topical application of from 1 to 5 g daily containing from 0.02 to 5 mg of the hair growth factor over the period of about two months will in most cases result in an improvement in hair growth.

EVALUATION OF EFFICACY OF HAIR GROWTH FACTORS USING THE RAT MODEL

The Rat Hair Growth Test

The effect of compounds on hair growth was assessed using male albino Wistar rats as an animal model. The rats were chosen from as few litters as possible and were each approximately 42 days of age at the start of the test. Each rat was housed individually to prevent licking.

In each comparison, 10 rats were used in each group and hair growth was assessed as follows:

A small patch of normal skin (4cm x 4cm) on the upper back of each rat was clipped at the start and 0.3 ml of a hair growth stimulant composition (or a control) applied topically twice daily and once on Saturdays and Sundays to each clipped area. The concentration of test compound in the composition was 0.2 mg/ml.

Hair was clipped from the area of the patch twice weekly, collected and weighed at each time point over a standard period of 3 months, and cumulative hair weight calculated. From these data, it was possible to estimate the effect of a hair growth stimulant as a test compound on the amount and duration of hair growth during the experiment. A positive response, i.e. an increase of at least 10% by weight of hair after 3 months treatment, compared with a control indicates the potential of the test compound to prevent hair loss and/or reverse baldness in human subjects.

Accordingly, when the growth factors, as herein defined, are assessed either individually or in combination as test compounds by the Rat Hair Growth Test, an increase of at least 10% by weight of hair after 3 months treatment will be obtained. Usually, the 10% by weight minimum value will be attained well before the end of this 3 month period.

EVALUATION OF THE EFFICACY OF HAIR GROWTH FACTORS USING A MITOGENISIS ASSAY

There are several biological assays which can be used to assess the biological activities of the hair growth factors. A preferred assay is the mitogenisis assay, which assesses the ability of the hair growth factors to stimulate DNA synthesis in a test cell line (NIH-3T3).

According to this assay, test cells are rendered quiescent in low serum medium (DMEM +L-glutamine +0.2 to 0.5% foetal calf serum) for 24 to 48 hours and the ability of the hair growth factors to increase the uptake of tritiated thymidine into DNA is assessed over a 24 hour period.

Addition of the hair growth factors, either individually or in combination in the preferred amounts as stated hereinbefore, stimulates an increase in the uptake of tritiated thymidine into DNA by at least 10% over the background level in the absence of added hair growth factors, by the end of the standard 24 hour period.

The hair growth factors identified in and isolated from the culture supernatant harvested from cultured dermal papilla cells, as stated earlier, are also able to stimulate cell proliferation of the test cell line either individually or in combination.

A positive response, i.e. an increase of at least 10% in the uptake of tritiated thymidine into DNA compared with a control is indicative of the potential of the test substance to prevent hair loss and/or reverse baldness in human subjects.

EXAMPLES

The invention is illustrated by the following examples.

EXAMPLE 1

This Example illustrates a lotion according to the invention which is suitable for topical application to the scalp in order to promote hair growth.

The lotion has the following formulation:

|  | % w/v |
|---|---|
| Hair growth factor: TGF-α | 0.0005 |
| preservative | 2 |
| perfume | q.s. |
| water | to 100 |

EXAMPLE 2

This example illustrates a hair tonic which is suitable for application to hair or scalp.

|  | % w/w |
|---|---|
| Hair growth factor: TGF-β | 0.000002 |
| ethanol | 5 |
| perfume | q.s. |
| water | to 100 |

EXAMPLE 3

This Example also illustrates a lotion which is suitable for topical application to the scalp.

The lotion has the following formulation:

|  | % w/v |
|---|---|
| Hair growth factor: IGF-1 | 0.000007 |
| propan-2-ol | 1 |
| ethanol | 4 |
| perfume | q.s. |
| Water | to 100 |

EXAMPLE 4

This Example also illustrates a hair tonic which is suitable for application to hair or scalp.

The hair tonic has the following formulation:

|  | % w/v |
|---|---|
| Hair growth factor: | |
| TGF-α | 0.000005 |
| IGF-I | 0.000007 |
| ethanol | 5 |
| perfume | q.s. |
| water | to 100 |

EXAMPLE 5

The following formulation represent a lotion which can be used topically in the treatment of bald or balding male or female heads.

|  | % w/v |
|---|---|
| Hydroxyethyl cellulose | 0.4 |

-continued

|  | % w/v |
| --- | --- |
| Absolute ethanol | 5 |
| Butane-1,3-diol | 38.4 |
| Paramethyl benzoate | 0.2 |
| Hair growth factor: | |
| TGF-α | 0.000005 |
| TGF-β | 0.000001 |
| IGF-1 | 0.000005 |
| Perfume | 1 |
| Water | to 100 |

EXAMPLE 6

The following formulation also represent a lotion which can be used topically in the treatment of bald or balding male or female heads.

|  | % w/v |
| --- | --- |
| Hydroxyethyl cellulose | 0.4 |
| Absolute ethanol | 5 |
| Butane-1,3-diol | 38.4 |
| Paramethyl benzoate | 0.2 |
| Hair growth factor: | |
| TGF-α | 0.000005 |
| TGF-β | 0.000001 |
| IGF-1 | 0.000005 |
| Minoxidil | 0.1 |
| Perfume | 1 |
| Water | to 100 |

What is claimed is:

1. A composition suitable for topical application to mammalian skin or hair which comprises:
   (a) a growth factor chosen from:
      (i) transforming growth factor alpha (TGF-α),
      (ii) transforming growth factor beta (TGF-β),
      (iii) insulin-like growth factor-1 (IGF-1),
      (iv) fragments thereof of one or more of said growth factors, and
      (v) mixtures thereof of said growth factors or fragments of said growth factors; and
   (b) a cosmetically acceptable vehicle for the growth factor or fragments thereof;
the total amount of growth factor being sufficient to increase hair growth in the rat, when the composition is applied topically thereto over a period of no more than 3 months, by at least 10% more than that obtainable using a control composition from which the said growth factor has been omitted, in accordance with the Rat Hair Growth Test.

2. The composition of claim 1, wherein the growth factor forms from 0.0002 to 10 mg/ml.

3. The composition of claim 2, which comprises from 0.0005 to 30 μg/ml of TGF-α.

4. The composition of claim 1, which comprises from 0.0002 to 20 μg/ml of TGF-β.

5. The composition of claim 1, which comprises from 0.0002 to 70 μg/ml of IGF-1.

6. The composition of claim 1, further comprising a protein stabilizing agent present in an effective amount for enhancing the activity of said growth factor which is selected from the group consisting of:
glycerol
ethylenediaminetetraacetic acid
cysteine
α₂-macroglobulin
serum
and mixtures thereof.

7. The composition of claim 1, further comprising means for enhancing the activity of said growth factor which is an iontophoretic device comprising a pad of absorbent material impregnated with a solution containing said growth factors.

8. A method for converting vellus hair to growth as terminal hair, which comprises the step of applying to the scalp in the region of vellus hair an effective amount of the composition of claim 1.

9. A method for increasing the rate of terminal hair growth, which comprises the step of applying to the scalp in the region of terminal hair an effective amount of the composition of claim 1.

10. The composition of claim 1 additionally comprising a hair growth stimulant in an effective amount for enhancing the activity of said growth factor selected from the group consisting of:
   (i) —1,4 esterified disaccharides having the structure (1):

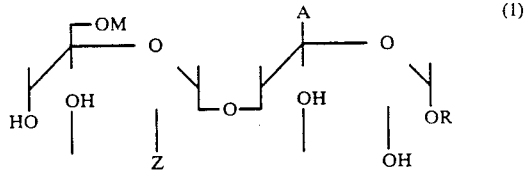

where
Z represents a functional nitrogen group, such as an azide or a group having the structure —NHB, in which B represents —H or a functional group such as acetyl or sulphate as a salt with an organic or mineral cation;
M represents —H or SO₃M₁, where M₁ is an organic or metallic cation or an acetyl group;
R represents a C₁ to C₄ alkyl radical or an aryl radical;
A represents a functional group such as an acid or —COOR₁, where R₁ represents —H or a C₁ to C₄ alkyl radical or a metal;
   (ii) esterified oligosaccharieds including at least one esterified disaccharide unit consisting of uronic acid residue having the structure (2) and a hexosamine residue having the structure (3);

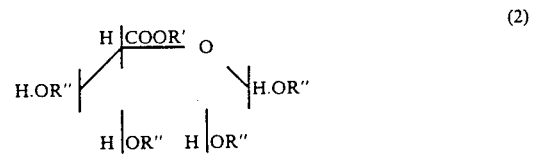

and a hexosamine residue having the structure (3):

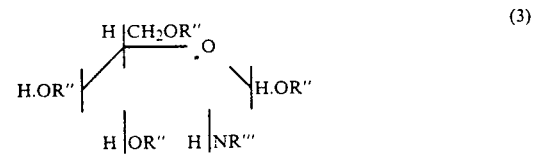

where
R' is C₃ to C₁₀ alkyl or $$-\overset{\text{COOR''}}{\underset{|}{\text{CH}}}(\text{CH}_2)_n\text{CH}_3$$

R" is —H, C$_1$ to C$_4$ alkyl, —CO(CH$_2$)$_m$CH$_3$, —SO$_3$M',
R''' is —H, —CO(CH$_2$)$_m$CH$_3$, or —SO$_3$M',
M' is —H, or a metallic or organic cation
n is 0 or an integer of from 1 to 7, and
m is 0 or the integer 1 or 2;

the groups designated R" being the same or different, one R" group from each pyranose ring structure being linked by a glycosidic linkage having the configuration α-1,3, α-1,4, β-1,3 or β-1,4; and the —COOR', —CH$_2$OR" and —OR" groups being of either configuration with respect to the pyranose rings;

(iii) 6-amino-1,2-dihydro-1-hydroxy-2-imino-4-piperidinopyrimidine;
(iv) 6-amino-1,2-dihydro-1-hydroxy-2-imino-4-piperidinopyrimidine glucoronide;
(v) 6-amino-1,2-dihydro-1-hydroxy-2-imino-4-piperidinopyrimidine sulphates;
(vi) 1,10-phenanthroline;
(vii) glycosaminoglycanase inhibitors having the structure (5) and (6):

$$\begin{array}{c} A^1 \\ | \\ B-C^2-H \\ | \\ B-C^3-H \\ | \\ B-C^4-H \\ | \\ B-C^5-H \\ | \\ A^6 \end{array} \quad (5)$$

$$\begin{array}{c} C^1HO \\ | \\ H-C^2-A \\ | \\ H-C^3-OG \\ | \\ H-C^4-OG \\ | \\ H-C^5-OG \\ | \\ CH_2G' \end{array} \quad (6)$$

where
A is —OG or —NHCOCH$_3$
G is —H, —SO$_3$M", C$_2$ to C$_4$ acyl
G' is —H or —OG
M" is —H or a metal cation (viii) glycosaminoglycanase chain cellular uptake inhibitors having the structure (7):

$$\begin{array}{c} C^1HO \\ | \\ H-C^2-OG \\ | \\ H-C^3-OG \\ | \\ H-C^4-OG \\ | \\ H-C^5-OG \\ | \\ C^6O_2D \end{array} \quad (7)$$

where
G is —H, —SO$_3$M", C$_2$ to C$_4$ acyl;
D is —H or C$_2$ to C$_8$ alkyl

M" is —H or a metal cation;
wherein the functional groups can be in either configuration with respect to the backbone of the above molecule;

(ix) glycosidase inhibitors having the structure (8):

$$\begin{array}{c} A^6 \\ | \\ Q-C^5-H \\ | \\ Q-C^4-H \\ | \\ Q-C^3-H \\ | \\ Q-C^2-H \\ | \\ A^1 \end{array} \quad (8)$$

where
A$^1$ and A$^6$ are —H, —CH$_3$, $$-\overset{\text{OT}}{\underset{|}{\text{C}}}=\text{O},$$

—CH$_2$OT or $-\overset{-\text{NH}}{\underset{|}{\text{C}}}=\text{O},$

A$^1$ and A$^6$ being the same or different, and at least one of which being the group;

$$\begin{array}{c} -\text{NH} \\ | \\ -\text{C}=\text{O} \end{array}$$

in a lactum ring;
and where
Q is —OT', —NHT' or a lactam linkage to A$^1$ or A$^6$; the Q groups being the same or different, and at least one of which is involved in a lactam linkage; and where
T is the same or different and is chosen from —H, —C$_p$H$_{2p+1}$ or a metal ion,
T' is —H or —COC$_p$H$_{2p+1}$, and
p is an integer of from 1 to 22;
provided that:
where any of the Q groups is —OT' or —NHT', then that group or groups can be of either stereochemical configuration with respect to the plane of the ring;

(x) chemical activators of protein kinase C having the structure (9):

$$\begin{array}{c} H_2-C-OH \\ | \\ H-C-OX \\ | \\ H_2-C-OX \end{array} \quad (9)$$

where
X is the same or different and is represented by the grouping:

$$\overset{\text{O}}{\underset{\|}{-\text{C}}}-[(\text{CH}_2)_x, (\text{CH}=\text{CH})_y]\text{CH}_3$$

where
x is 0 or an integer of from 1 to 28, and y is 0 or an integer of from 1 to 5;
the OX groups being of either stereochemical configuration with respect to the carbon backbone of the glycerol molecule, the double bonds being of either cis or trans configuration; and
(xi) mixtures thereof.

11. The composition of claim 10, wherein the hair growth stimulant is 6-amino-1,2-dihydro-1-hydroxy-2-imino-4-piperidinopyrimidine.

12. The composition of claim 10, wherein the glycosaminoglycanase inhibitor is an aldonolactone or an esterified aldonolactone having structure (5).

13. The composition of claim 10, wherein the glycosaminoglycanase inhibitor is a monosacchride or an esterified mnosaccharide having structure (6).

14. The composition of claim 10, wherein the glycosidase inhibitor is a lactam having the structure (8).

15. The composition of claim 10, wherein the chemical activator of protein kinase C is a diacylglycerol having the structure (9).

16. The composition of claim 1, further comprising a means for enhancing the activity of said growth factor with a penetration enhancer which is selected from the group consisting of:
1-dodecylazacycloheptan-2-one,
dibutyl sebacate,
2-hydroxyoctanoic acid,
esters of pyroglutamic acid having the structure (10)

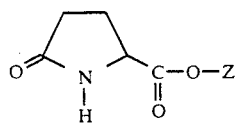

(10)

where
Z is C$_1$ to C$_{30}$ alkyl, or

—CHCOOZ'' and where
Z' and Z'' are the same or different and are each represented by H or the grouping (11):

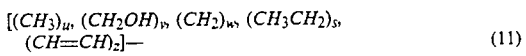

(11)

where
u is zero or 1
v is zero, or the integer of from 1 to 2,
w is zero, or an integer of from 1 to 21
s is zero, or an integer of from 1 to 4,
y is zero, or the integer 1 or 2,
z is zero, or an integer of from 1 to 22, and
u+v+w+x+y+z is an integer of from 1 to 22;
provided that when the subgrouping (CH=CH) is present, then the total number of carbon atoms in said grouping is from 10 to 22, and mixtures thereof.

17. The composition of claim 1, further comprising a penetration enhancer present in an effective amount for enhancing the activity of said growth factor which is a surface active agent selected from the group consisting of anionic, cationic, amphoteric and nonionic wetting agents.

18. The composition of claim 1, further comprising an effective amount for enhancing the activity of said growth factor of a cationic polymer selected from the group consisting of:
Guar Hydroxypropyltrimonium chloride
Quaternium-19
Quaternium-23
Quaternium-40
Quaternium-57
Poly(dipropyldiallylammonium chloride)
Poly(methyl-β-propaniodiallylammonium chloride)
Poly(diallylpiperidinium chloride)
Poly(vinyl pyridinium chloride)
Quaternized poly (vinyl alcohol)
Quaternized poly (dimethylaminoethylmethacrylate); and
mixtures thereof.

* * * * *